(12) United States Patent
Ross et al.

(10) Patent No.: US 10,918,407 B2
(45) Date of Patent: Feb. 16, 2021

(54) SURGICAL INSTRUMENT FOR GRASPING, TREATING, AND/OR DIVIDING TISSUE

(71) Applicant: COVIDIEN LP, Mansfield, MA (US)

(72) Inventors: Anthony B. Ross, Boulder, CO (US); Eric R. Larson, Boulder, CO (US); Michael B. Lyons, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 491 days.

(21) Appl. No.: 15/798,465

(22) Filed: Oct. 31, 2017

(65) Prior Publication Data

US 2018/0125518 A1 May 10, 2018

Related U.S. Application Data

(60) Provisional application No. 62/419,018, filed on Nov. 8, 2016.

(51) Int. Cl.
*A61B 17/295* (2006.01)
*A61B 17/32* (2006.01)
(Continued)

(52) U.S. Cl.
CPC ............ *A61B 17/295* (2013.01); *A61B 17/29* (2013.01); *A61B 17/3211* (2013.01); *A61B 17/320016* (2013.01); *A61B 18/1445* (2013.01); *A61B 17/2909* (2013.01); *A61B 2017/2946* (2013.01); *A61B 2018/00922* (2013.01); *A61B 2018/00946* (2013.01); *A61B 2018/00952* (2013.01);
(Continued)

(58) Field of Classification Search
CPC ........ A61B 18/1442; A61B 2018/0094; A61B 2018/00946; A61B 2018/00952; A61B 2018/00958; A61B 2018/1452; A61B 2018/1455
See application file for complete search history.

(56) References Cited

U.S. PATENT DOCUMENTS 371,664 A 10/1887 Brannan et al.
702,472 A 6/1902 Pignolet
(Continued)

FOREIGN PATENT DOCUMENTS

CA 2104423 A1 2/1994
DE 2415263 A1 10/1975
(Continued)

*Primary Examiner* — Ronald Hupczey, Jr.
(74) *Attorney, Agent, or Firm* — Carter, DeLuca & Farrell LLP

(57) ABSTRACT

A surgical instrument includes a shaft extending distally from the housing, an end effector assembly disposed at a distal end of the shaft and configured to supply energy to tissue to treat tissue, a knife slidably disposed within the shaft and movable relative to the end effector assembly between a retracted position and an extended position, and a trigger operably coupled to the housing. The trigger is selectively activatable from a neutral position to a laterally pivoted position to supply energy to the end effector assembly and is selectively actuatable from a distal position to a proximally pivoted position to deploy the knife from the retracted position to the extended position. In the laterally pivoted position of the trigger, actuation of the trigger is inhibited. In the proximally pivoted position of the trigger, activation of the trigger is inhibited.

20 Claims, 11 Drawing Sheets

(51) Int. Cl.
*A61B 17/29* (2006.01)
*A61B 17/3211* (2006.01)
*A61B 18/00* (2006.01)
*A61B 18/14* (2006.01)

(52) U.S. Cl.
CPC .............. *A61B 2018/00958* (2013.01); *A61B 2018/1455* (2013.01)

(56) References Cited

U.S. PATENT DOCUMENTS

| | | | |
|---|---|---|---|
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,688,538 A | 9/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,862,830 A | 1/1975 | Stern |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,937,222 A | 2/1976 | Banko |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,167,944 A | 9/1979 | Banko |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| D276,790 S | 12/1984 | Laske |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,850,354 A | 7/1989 | McGurk-Burleson et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,007,917 A | 4/1991 | Evans |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,106,364 A | 4/1992 | Hayafuji et al. |
| 5,116,332 A | 5/1992 | Lottick |
| 5,146,921 A | 9/1992 | Terwilliger et al. |
| 5,147,357 A | 9/1992 | Rose et al. |
| 5,151,102 A | 9/1992 | Kamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,609 A | 1/1994 | Pingleton et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,312,423 A | 5/1994 | Rosenbluth et al. |
| 5,312,433 A | 5/1994 | Boebel et al. |
| 5,314,445 A | 5/1994 | Heidmueller et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,409,013 A | 4/1995 | Clement |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |

(56) References Cited

U.S. PATENT DOCUMENTS

| | | |
|---|---|---|
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Shame et al. |
| 5,509,922 A | 4/1996 | Aranyi et al. |
| 5,514,134 A | 5/1996 | Rydell et al. |
| 5,527,313 A | 6/1996 | Scott et al. |
| 5,527,332 A | 6/1996 | Clement |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,693 A | 7/1996 | Fisher |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,730,752 A | 3/1998 | Alden et al. |
| 5,735,848 A | 4/1998 | Yates et al. |
| 5,741,287 A | 4/1998 | Alden et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,647 A | 7/1998 | Chau et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,083 A | 10/1998 | Shemesh et al. |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,873,886 A | 2/1999 | Larsen et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,925,056 A | 7/1999 | Thomas et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,964,777 A | 10/1999 | Drucker |
| 5,976,132 A | 11/1999 | Morris |
| 5,984,939 A | 11/1999 | Yoon |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka |
| 6,024,741 A | 2/2000 | Williamson, IV et al. |
| 6,024,744 A | 2/2000 | Kese et al. |
| 6,030,384 A | 2/2000 | Nezhat |

(56) References Cited

U.S. PATENT DOCUMENTS

| | | |
|---|---|---|
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,159,179 A | 12/2000 | Simonson |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,299,625 B1 | 10/2001 | Bacher |
| 6,302,424 B1 | 10/2001 | Gisinger et al. |
| 6,319,451 B1 | 11/2001 | Brune |
| 6,322,561 B1 | 11/2001 | Eggers et al. |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,747,218 B2 * | 6/2004 | Huseman ............ H01H 13/7006 200/1 B |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |

(56) References Cited

U.S. PATENT DOCUMENTS

| | | |
|---|---|---|
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 8,192,433 B2 | 6/2012 | Johnson et al. |
| 8,540,711 B2 | 9/2013 | Dycus et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0193153 A1 | 9/2004 | Sartor et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0169981 A1 | 8/2006 | Joo |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0287641 A1 | 12/2006 | Perlin |
| 2007/0016182 A1 | 1/2007 | Lipson et al. |
| 2007/0016187 A1 | 1/2007 | Weinberg et al. |

(56) References Cited

U.S. PATENT DOCUMENTS

| | | |
|---|---|---|
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2013/0267975 A1* | 10/2013 | Timm ............ A61B 17/320092 606/169 |
| 2014/0031819 A1* | 1/2014 | Dycus ................ A61B 18/1445 606/47 |
| 2014/0148803 A1* | 5/2014 | Taylor ................ A61B 18/1445 606/34 |
| 2015/0250531 A1 | 9/2015 | Dycus et al. |

FOREIGN PATENT DOCUMENTS

| | | |
|---|---|---|
| DE | 2627679 A1 | 1/1977 |
| DE | 8712328 U1 | 2/1988 |
| DE | 04303882 C2 | 2/1995 |
| DE | 29616210 U1 | 11/1996 |
| DE | 19608716 C1 | 4/1997 |
| DE | 19751106 A1 | 5/1998 |
| DE | 19751108 A1 | 5/1999 |
| EP | 0541930 A1 | 5/1993 |
| EP | 0572131 A1 | 12/1993 |
| EP | 0584787 A1 | 3/1994 |
| EP | 0589453 A3 | 4/1994 |
| EP | 0624348 A3 | 6/1995 |
| EP | 0364216 B1 | 1/1996 |
| EP | 0518230 B1 | 5/1996 |
| EP | 0541930 B1 | 3/1998 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 | 7/2003 |
| EP | 1330991 A1 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1609430 | 12/2005 |
| EP | 1609430 A1 | 12/2005 |
| EP | 1034746 B1 | 3/2006 |
| EP | 1632192 | 3/2006 |
| EP | 1645238 | 4/2006 |
| EP | 1645238 A1 | 4/2006 |
| EP | 1645240 | 4/2006 |
| EP | 1645240 A2 | 4/2006 |
| EP | 0875209 B1 | 5/2006 |
| EP | 1707143 | 10/2006 |
| EP | 1707143 A1 | 10/2006 |
| GB | 2213416 A | 8/1989 |
| GB | 2214430 A | 9/1989 |
| JP | 61-501068 | 9/1984 |
| JP | 6-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | H08-56955 | 5/1996 |
| JP | 08252263 A | 10/1996 |
| JP | 910223 | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 89/00757 | 1/1989 |
| WO | 92/04873 | 4/1992 |
| WO | 92/06642 | 4/1992 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 96/05776 | 2/1996 |
| WO | 96/022056 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/24073 | 7/1997 |
| WO | 97/24993 | 7/1997 |
| WO | 9727880 A1 | 8/1997 |
| WO | 98/27880 | 7/1998 |
| WO | 9827860 A2 | 7/1998 |
| WO | 99/03407 | 1/1999 |
| WO | 99/03408 | 1/1999 |
| WO | 99/03409 | 1/1999 |
| WO | 9903409 A1 | 1/1999 |
| WO | 99/12488 | 3/1999 |
| WO | 99/40857 | 8/1999 |
| WO | 99/40861 | 8/1999 |
| WO | 9940881 A2 | 8/1999 |
| WO | 99040861 A1 | 8/1999 |

(56) References Cited

FOREIGN PATENT DOCUMENTS

| | | |
|---|---|---|
| WO | 99/51158 | 10/1999 |
| WO | 99/66850 | 12/1999 |
| WO | 9966850 A1 | 12/1999 |
| WO | 00/24330 | 5/2000 |
| WO | 00/24331 | 5/2000 |
| WO | 00/41638 | 7/2000 |
| WO | 00/47124 | 8/2000 |
| WO | 00/53112 | 9/2000 |
| WO | 01/17448 | 3/2001 |
| WO | 0154604 A1 | 8/2001 |
| WO | 02/07627 | 1/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080794 | 10/2002 |
| WO | 02/080795 | 10/2002 |
| WO | 02/080796 | 10/2002 |
| WO | 02/080797 | 10/2002 |
| WO | 02/080798 | 10/2002 |
| WO | 02/080799 | 10/2002 |
| WO | 02/080799 A1 | 10/2002 |
| WO | 02/081170 | 10/2002 |
| WO | 02080763 A2 | 10/2002 |
| WO | 02080793 A1 | 10/2002 |
| WO | 02080796 A1 | 10/2002 |
| WO | 03/101311 | 12/2003 |
| WO | 03/090630 A3 | 4/2004 |
| WO | 04/032777 | 4/2004 |
| WO | 2004/032776 A1 | 4/2004 |
| WO | 2004/032777 A1 | 4/2004 |
| WO | 2004/052221 A1 | 6/2004 |
| WO | 04/073490 A2 | 9/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004/098383 A2 | 11/2004 |
| WO | 04096383 A1 | 11/2004 |
| WO | 04/103156 | 12/2004 |
| WO | 2004/103156 A2 | 12/2004 |
| WO | 2005/004734 A1 | 1/2005 |
| WO | 2005/004735 A1 | 1/2005 |
| WO | 05110264 A3 | 4/2006 |

* cited by examiner

SURGICAL INSTRUMENT FOR GRASPING, TREATING, AND/OR DIVIDING TISSUE

CROSS REFERENCE TO RELATED APPLICATION

The present application claims the benefit of and priority to U.S. Provisional Application Ser. No. 62/419,018, filed on Nov. 8, 2016 the entire contents of which are incorporated herein by reference.

BACKGROUND

Technical Field

The present disclosure relates generally to the field of surgical instruments. In particular, the disclosure relates to a surgical instrument for grasping, treating, and/or dividing tissue.

Background of Related Art

Various different surgical instruments are utilized for grasping, treating, and/or dividing tissue. A surgical forceps, for example, is a pliers-like surgical instrument that relies on mechanical action between its jaw members to grasp, clamp, and constrict tissue. Energy-based surgical forceps utilize both mechanical clamping action and energy, e.g., radiofrequency (RF) energy, microwave energy, ultrasonic energy, light energy, thermal energy, etc., to heat tissue to treat, e.g., coagulate, cauterize, and/or seal, tissue.

Typically, once tissue is treated, the surgeon has to accurately divide the treated tissue. Accordingly, many surgical forceps are designed to incorporate a knife or cutting member utilized to effectively divide the treated tissue.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein.

Provided in accordance with aspects of the present disclosure is a surgical instrument including a housing, a shaft extending distally from the housing, an end effector assembly disposed at a distal end of the shaft and adapted to connect to a source of energy to supply energy to tissue to treat tissue, a knife slidably disposed within the shaft and movable relative to the end effector assembly between a retracted position and an extended position, and a trigger operably coupled to the housing. The trigger is selectively activatable from a neutral position to a laterally pivoted position to supply energy to the end effector assembly, and selectively actuatable from a distal position to a proximally pivoted position to deploy the knife from the retracted position to the extended position. In the laterally pivoted position, actuation of the trigger is inhibited. On the other hand, in the proximally pivoted position, activation of the trigger is inhibited.

In an aspect of the present disclosure, the trigger includes a toggle and a disc body. The disc body is pivotably coupled to the housing to permit actuation of the trigger from the distal position to the proximally pivoted position. The toggle is pivotably coupled to the disc body and pivotable relative thereto for activating the trigger from the neutral position to the laterally pivoted position.

In another aspect of the present disclosure, the trigger is selectively activatable from the neutral position to first and second opposed laterally pivoted positions.

In still another aspect of the present disclosure, the trigger defines a distally-facing surface configured to facilitate manual manipulation of the trigger from the distal position to the proximally pivoted position. The trigger may further define a pair of side wing surfaces extending from opposing sides of the distally-facing surface and configured to facilitate manual manipulation of the trigger from the neutral position to the laterally pivoted position.

In yet another aspect of the present disclosure, the end effector assembly includes first and second jaw members. One or both of the jaw members is movable relative to the other between a spaced-apart position and an approximated position.

In still yet another aspect of the present disclosure, a movable handle is operably coupled to the housing and movable relative thereto between an initial position and a compressed position for moving the jaw members between the spaced-apart position and the approximated position.

In another aspect of the present disclosure, in the initial position of the movable handle, the movable handle interferes with the trigger to inhibit activation of the trigger from the neutral position towards the laterally pivoted position.

In another aspect of the present disclosure, an activation assembly including at least switch is disposed within the housing. The at least one switch is positioned such that, upon activation of the trigger from the neutral position to the laterally pivoted position, a portion of the trigger activates the at least one switch. The at least one switch may be a dome switch configured to produce at least one of an audible or tactile output in response to activation thereof.

Another surgical instrument provided in accordance with aspects of the present disclosure includes a housing, a shaft extending distally from the housing, an end effector assembly disposed at a distal end of the shaft, a movable handle operably coupled to the housing, a knife slidably disposed within the shaft, and a trigger operably coupled to the housing. The end effector assembly includes first and second jaw members adapted to connect to a source of energy to supply energy to tissue to treat tissue. One or both of the jaw members is movable relative to the other between a spaced-apart position and an approximated position. The movable handle is movable between an initial position and a compressed position to move the jaw members between the spaced-apart position and the approximated position. The knife is slidably disposed within the shaft and movable between a retracted position and an extended position, wherein the knife extends at least partially between the first and second jaw members. The trigger is laterally pivotable to supply energy to the first and second jaw members and proximally pivotable to move the knife from the retracted position to the extended position. In the initial position of the movable handle, at least a portion of the movable handle interferes with the trigger to inhibit lateral pivoting thereof.

In an aspect of the present disclosure, the trigger includes a toggle and a disc body. The disc body is pivotably coupled to the housing to permit proximal pivoting of the trigger, while the toggle is pivotably coupled to the disc body and pivotable relative thereto to permit lateral pivoting of the trigger.

In another aspect of the present disclosure, the trigger is laterally pivotable in either direction from a neutral position to a laterally pivoted position to supply energy to the first and second jaw members.

In another aspect of the present disclosure, the trigger defines a distally-facing surface configured to facilitate proximal pivoting of the trigger. The trigger may further define a pair of side wing surfaces extending from opposing sides of the distally-facing surface. The side wing surfaces are configured to facilitate lateral pivoting of the trigger. In the initial position of the movable handle, the side wing surfaces at least partially surround the movable handle.

In yet another aspect of the present disclosure, the surgical instrument further includes a drive assembly operably coupled between the end effector assembly and the movable handle such that movement of the movable handle from the initial position to the compressed position moves the jaw members from the spaced-apart position to the approximated position.

In still another aspect of the present disclosure, at least one linkage is operably coupled between the trigger and the knife such that proximal pivoting of the trigger moves the knife from the retracted position to the extended position.

In still yet another aspect of the present disclosure, the knife defines a distal cutting edge having a dual rake configuration.

In another aspect of the present disclosure, the surgical instrument further includes an activation assembly including at least switch disposed within the housing. The at least one switch is positioned such that, upon lateral pivoting of the trigger, the trigger activates the at least one switch to supply energy to the first and second jaw members.

In still another aspect of the present disclosure, a first portion of the housing interferes with the trigger to inhibit proximal pivoting of the trigger when the trigger is laterally pivoted, and a second portion of the housing interferes with the trigger to inhibit lateral pivoting of the trigger when the trigger is proximally pivoted.

BRIEF DESCRIPTION OF THE DRAWINGS

Various aspects and features of the present disclosure are described herein with reference to the drawings, wherein like reference numerals identify similar or identical components, and wherein.

DETAILED DESCRIPTION

Figure 1:
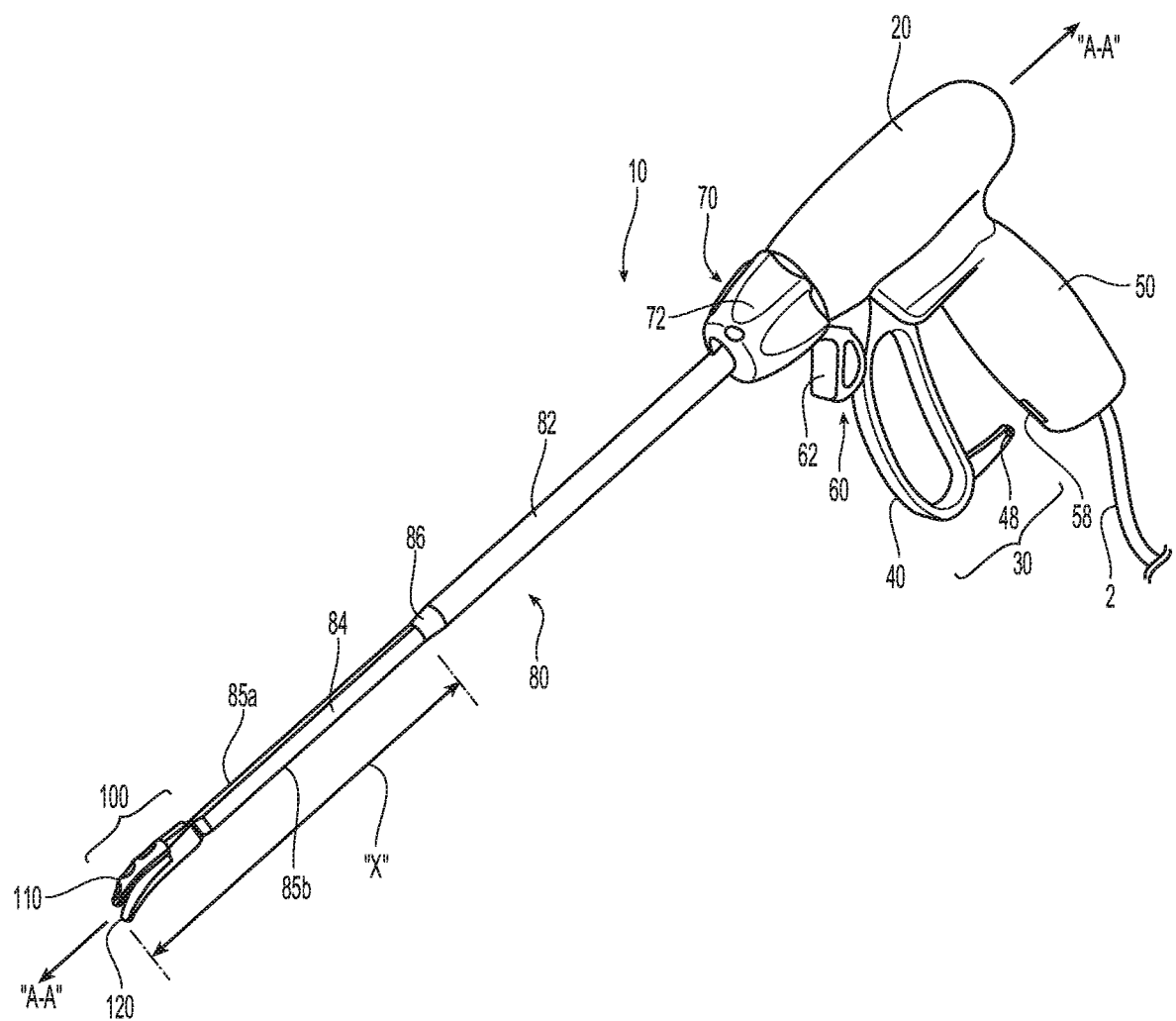
FIG. 1 is a perspective view of an endoscopic surgical forceps provided in accordance with aspects of the present disclosure.

Referring generally to FIG. 1, an endoscopic surgical forceps provided in accordance with the present disclosure is shown generally identified by reference numeral 10. As described in greater detail below, forceps 10 is configured for insertion through a cannula 200 (FIG. 2) and into an internal surgical site for grasping tissue, treating the grasped tissue with energy, and dividing the grasped and/or treated tissue. Although detailed herein with respect to endoscopic forceps 10, the aspects and features of the present disclosure are equally applicable for use with any suitable surgical instrument.

Figure 6A:
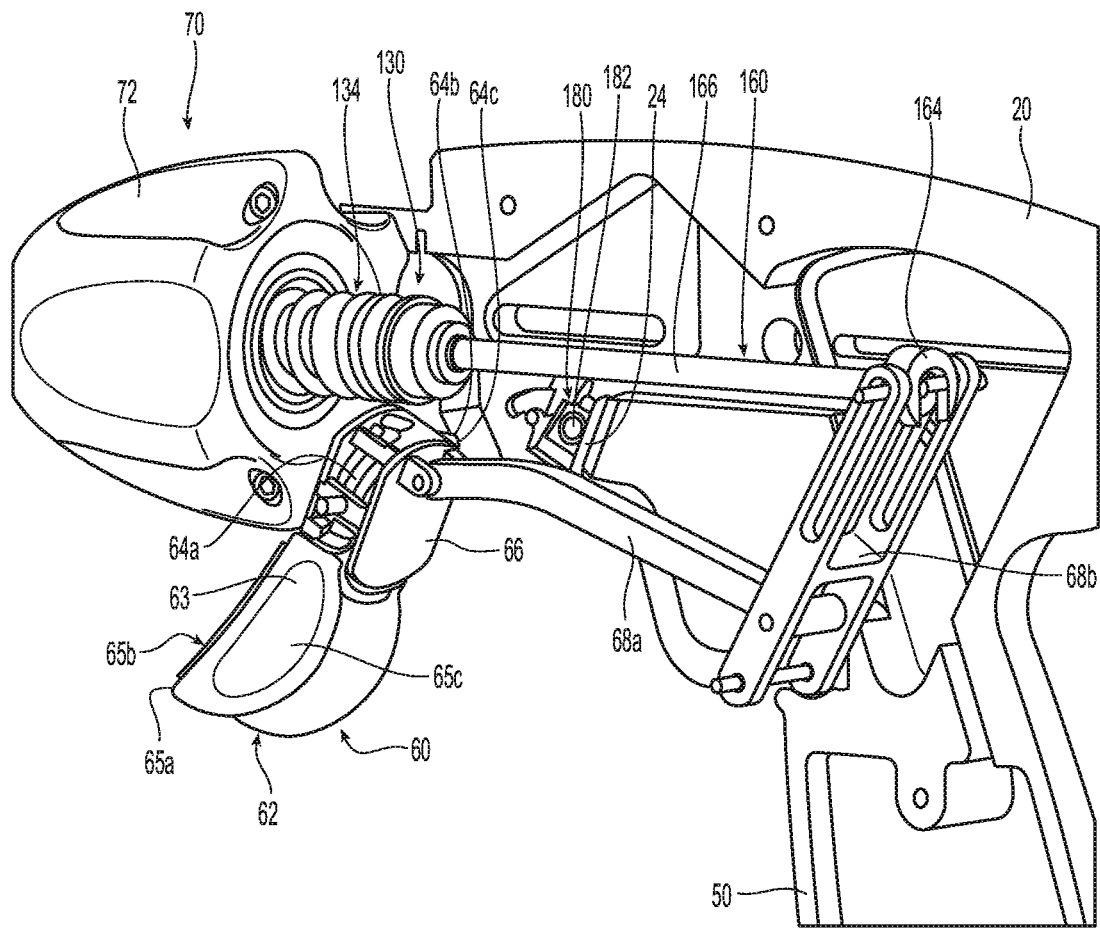
FIG. 6A is a perspective, exploded view of another proximal portion of the surgical forceps of FIG. 1, with components removed.
Figure 6B:
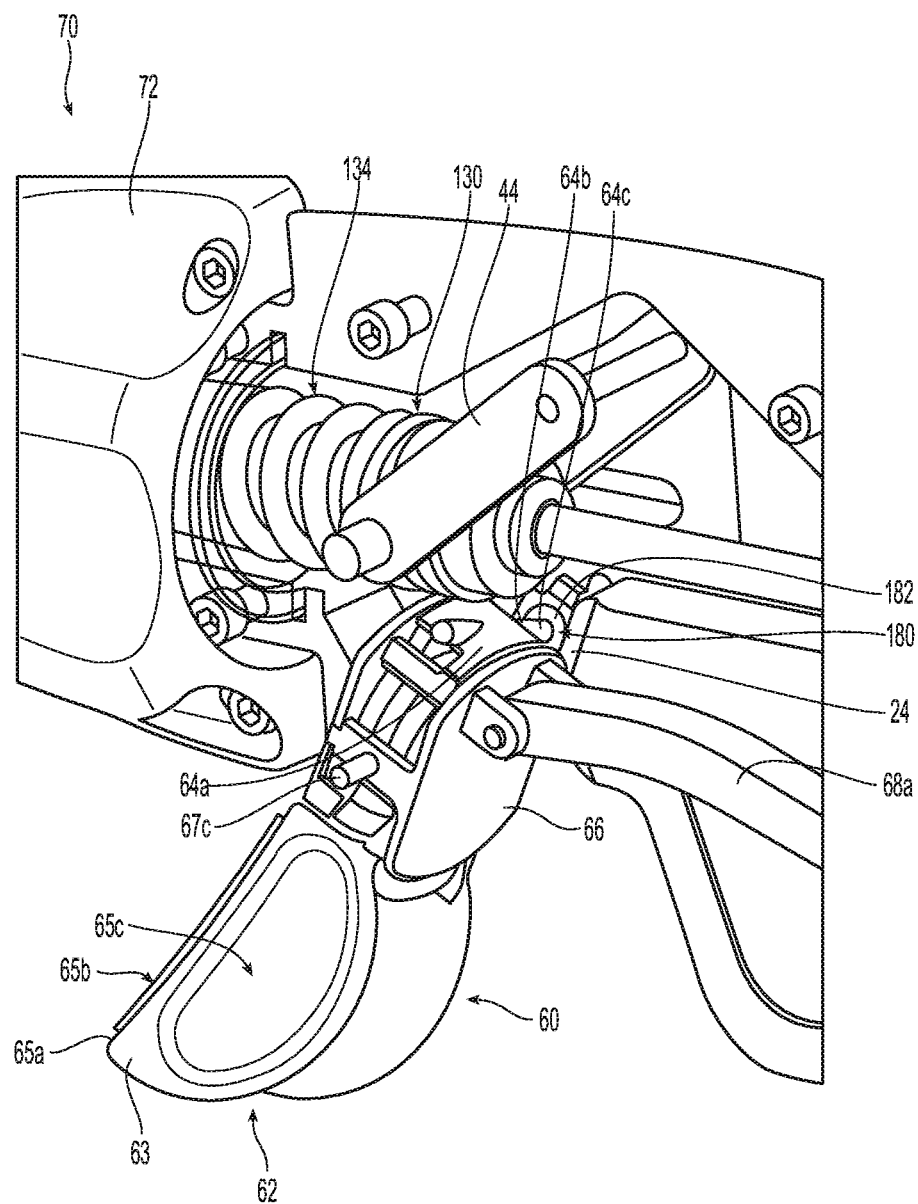
FIG. 6B is a perspective view of another proximal portion of the surgical forceps of FIG. 1, with components removed.
Figure 6C:
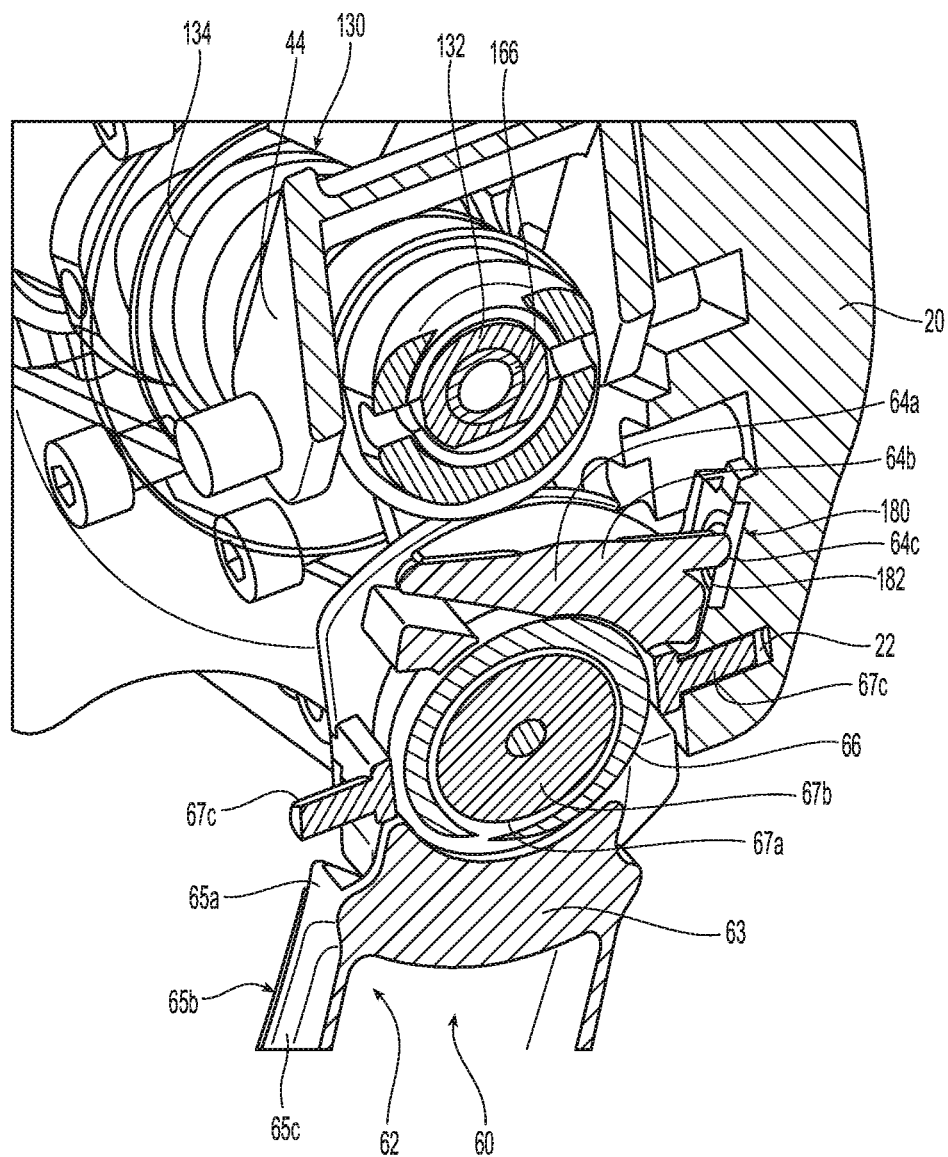
FIG. 6C is a perspective, transverse, cross-sectional view taken through another proximal portion of the surgical forceps of FIG. 1, with components removed.

With reference to FIGS. 1 and 4-8B, forceps 10 generally includes a housing 20, a handle assembly 30, a trigger assembly 60, a rotation assembly 70, a shaft 80, an end effector assembly 100, a drive assembly 130 (FIGS. 6A-6C), a knife assembly 160 (FIGS. 6A and 8B), and an activation assembly 180 (FIGS. 6A-6C). Forceps 10 further includes a cable 2 configured to couple forceps 10 to a source of energy, e.g., an electrosurgical generator (not shown), for supplying energy to end effector assembly 100, although forceps 10 may alternative be configured as a cordless, hand-held device. The components and assemblies of forceps 10 are described more generally, followed by a more detailed description of the components and assemblies of forceps 10 that are germane to the aspects and features of the present disclosure.

Handle assembly 30 is operably coupled to housing 20 and includes a movable handle 40 extending from housing 20 adjacent fixed handle portion 50 of housing 20 to permit manual manipulation of movable handle 40 by a user. Trigger assembly 60 is also operably coupled to housing 20 and similarly includes a trigger 62 extending from housing 20 to permit manual manipulation thereof by a user.

Shaft 80 extends distally from housing 20, defines a longitudinal axis "A-A," and includes end effector assembly 100 disposed towards the distal end thereof. Shaft 80 may be configured as an integral, rigid component. Rotation assembly 70 may be disposed about the distal end of housing 20 and operably coupled to shaft 80 such that rotation of rotation nose 72 of rotation assembly 70 rotates shaft 80 and end effector assembly 100 relative to housing 20.

End effector assembly 100 includes first and second jaw members 110, 120, at least one of which is movable relative to the other and shaft 80 between a spaced-apart position and an approximated position. Drive assembly 130 (FIGS. 6A-6C) extends through housing 20 and shaft 80 and operably couples movable handle 40 of handle assembly 30 with end effector assembly 100 such that movement of movable handle 40 moves jaw members 110, 120 between the spaced-apart and approximated positions.

Figure 8A:
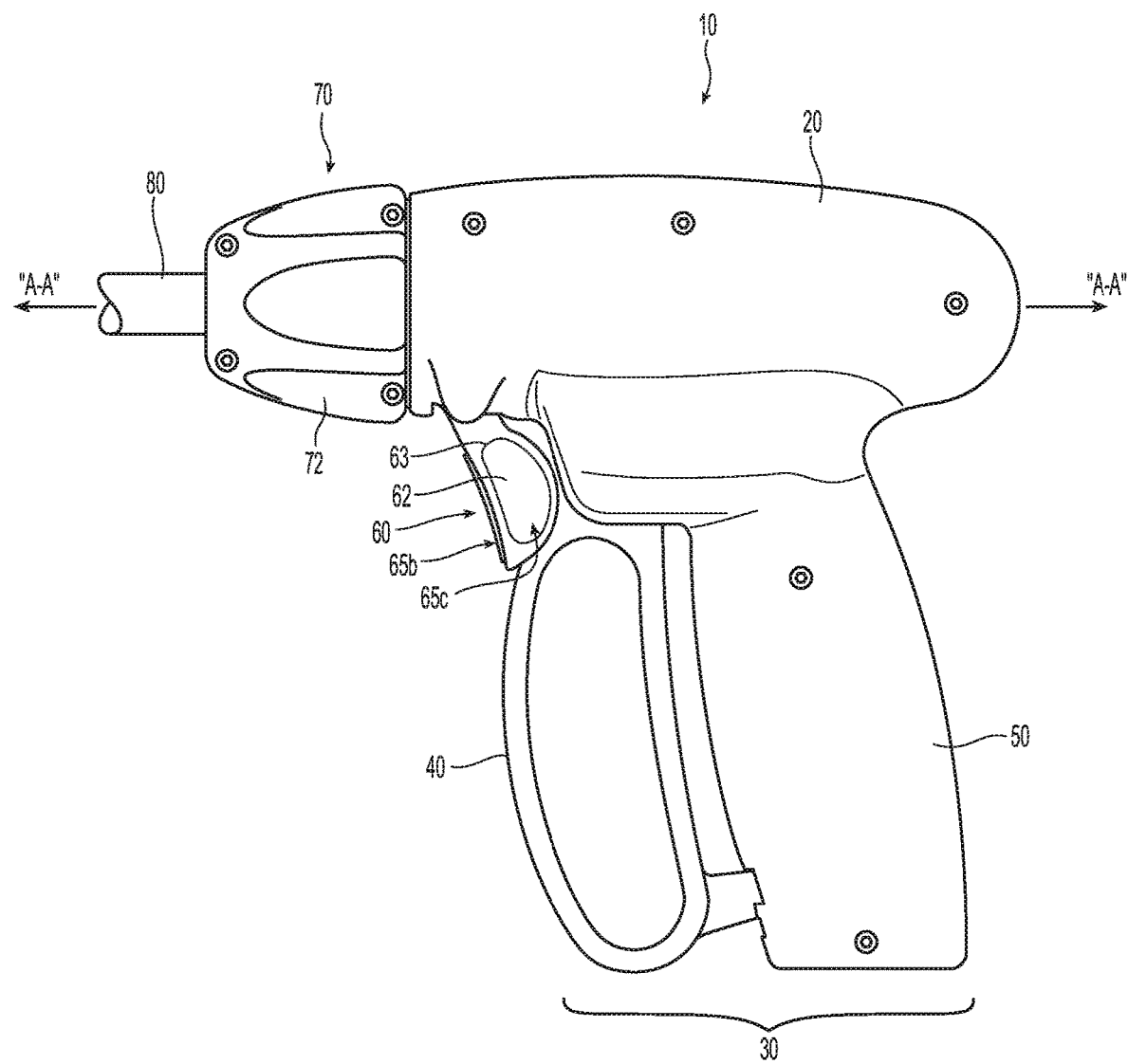
FIG. 8A is a side view of a proximal portion of the surgical forceps of FIG. 1, with the handle disposed in a compressed position and the trigger disposed in an actuated position.
Figure 8B:
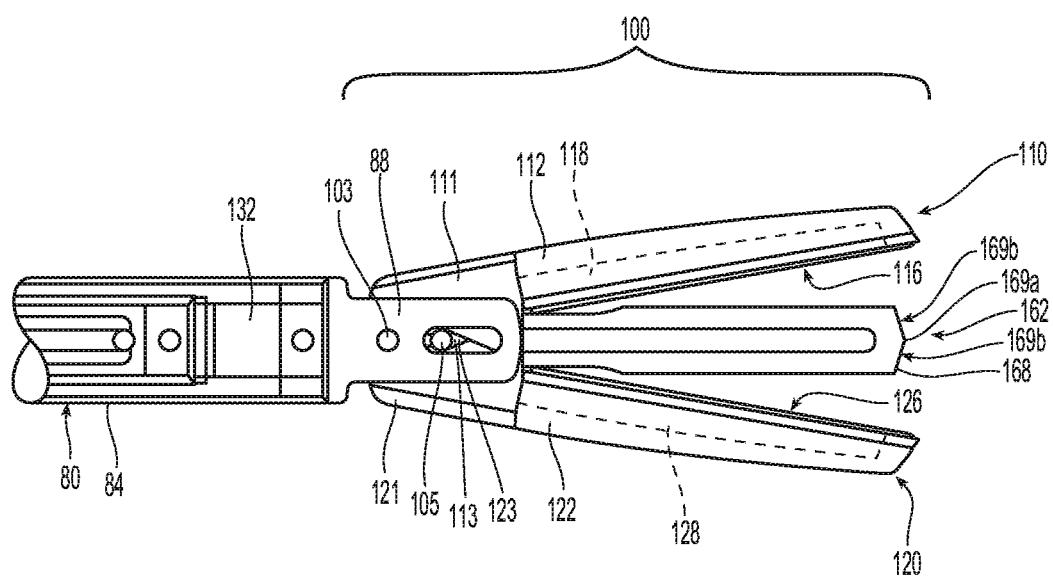
FIG. 8B is a side view of the end effector assembly of the surgical forceps of FIG. 1 with the knife disposed in an extended position corresponding to the actuated position of the trigger of FIG. 8A.

Knife assembly 160 (FIG. 6A) includes a knife 162 (FIG. 8B) slidably disposed within shaft 80 and operably coupled to trigger 62 of trigger assembly 60 such that actuation of trigger 62 advances knife 162 from a retracted position, wherein knife 162 is disposed proximally of end effector assembly 100, to an extended position, wherein knife 162 extends between jaw members 110, 120 (see FIG. 8B). With particular reference to FIG. 8B, knife 162 includes a distal cutting edge 168 having a dual-rake configuration defining a central protruding point 169a and angled cutting edges 169b angled proximally from central protruding point 169a. As a result of this configuration, upon advancement of knife 162, distal cutting edge 168 is led by central protruding point 169a, which is the distal-most portion of knife 162 and is positioned between jaw members 110, 120, while angled extend proximally from central protruding point 169a at least partially into the knife channels 118, 128 of jaw members 110, 120, respectively. It is noted that jaw members 110, 120 are shown in a partially-open condition in FIG. 8B to permit visualization of knife 162 and, thus, knife 162 is not shown positioned within knife channels 118, 128. However, with jaw members 110, 120 in the approximated position upon advancement of knife 162, the above-detailed configuration is achieved.

Referring again to FIGS. 1 and 4-8B, activation assembly 180 (FIGS. 6A-6C) includes a pair of switches 182 (FIGS. 6A-6C; only one switch 182 is shown) disposed within housing 20 and operably associated with trigger 62 of trigger assembly 60 such that activation of trigger 62 depresses one of switches 182 (depending upon the direction of activation of trigger 62) to supply energy from the energy source to jaw members 110, 120 of end effector assembly 100. Cable 2 includes a plurality of lead wires (not explicitly shown) extending therethrough. The lead wires extend through housing 20 and shaft 80 to electrically couple the energy source, switches 182 of activation assembly 180, and electrically-conductive surfaces 116, 126 of jaw members 110, 120 with one another.

Figure 2:
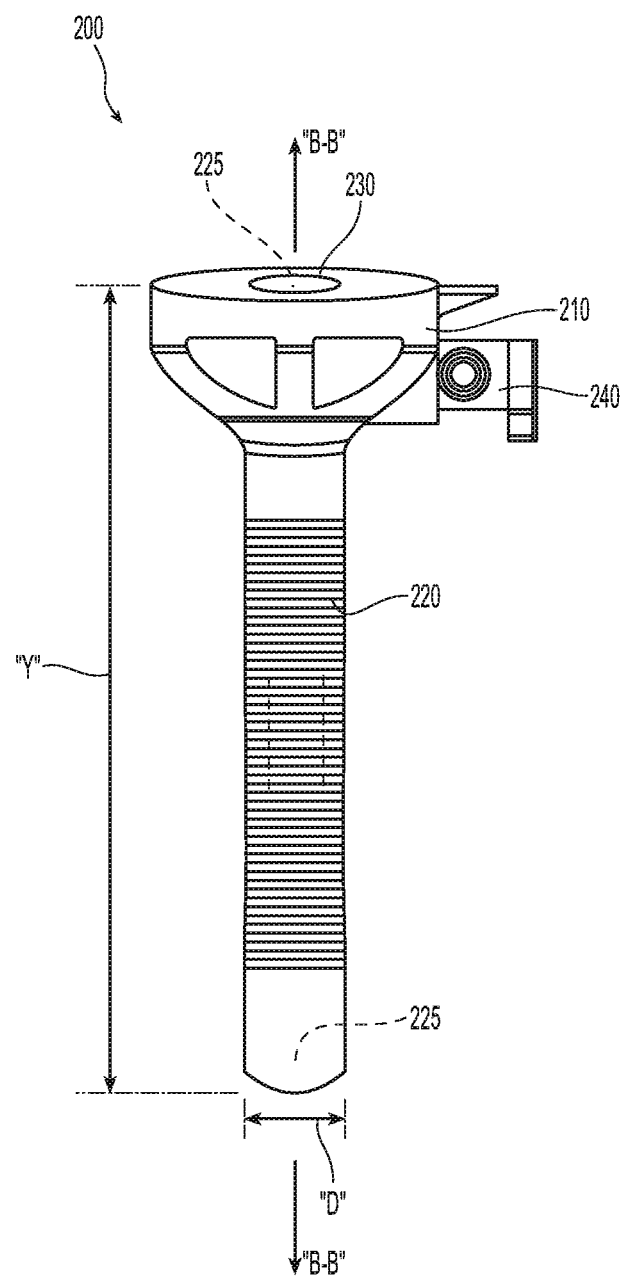
FIG. 2 is a perspective view of a cannula configured for use with the surgical forceps of FIG. 1.
Figure 3:
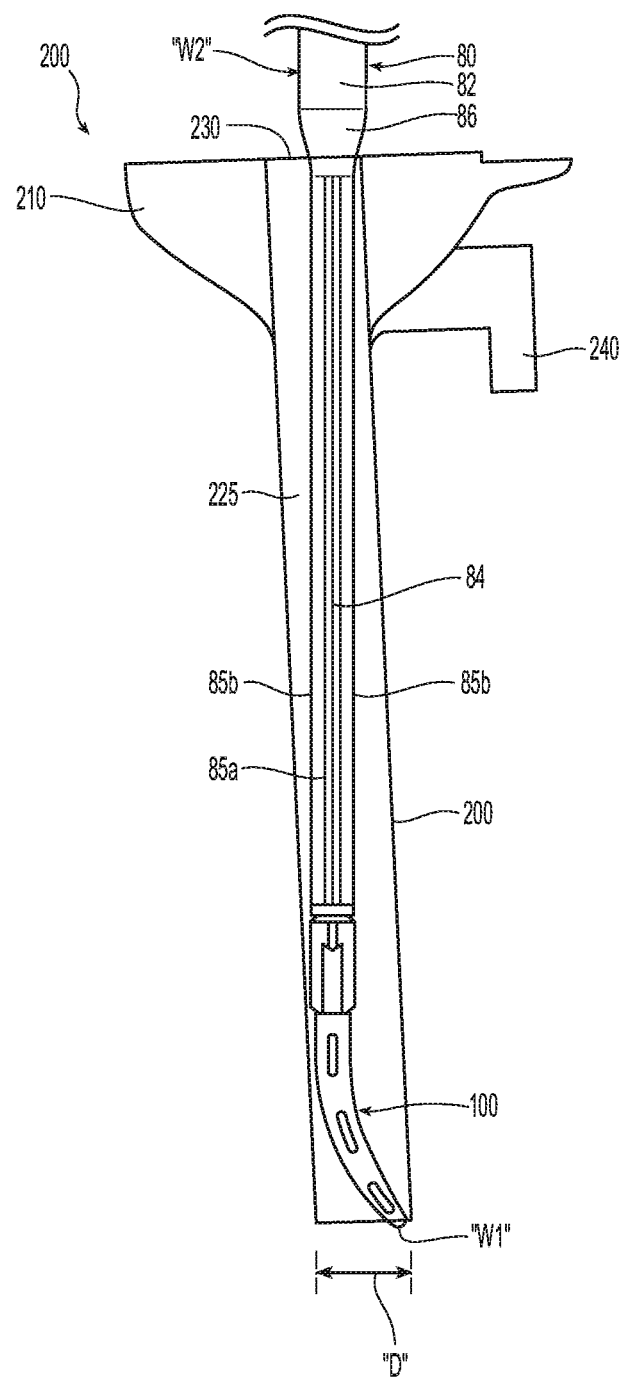
FIG. 3 is a side, partial cross-sectional view illustrating insertion of a distal portion of the surgical forceps of FIG. 1 through the cannula of FIG. 2.

With additional reference to FIGS. 2 and 3, forceps 10 is configured for use in endoscopic surgical procedures (although forceps 10 may equally be used in traditional open surgical procedures) and, thus, shaft 80 and jaw members 110, 120 of end effector assembly 100 are configured for insertion through a cannula 200 to facilitate access to an internal surgical site. Shaft 80 defines longitudinal axis "A-A" and includes a proximal portion 82, a distal portion 84, and a transition portion 86 between proximal and distal portions 82, 84 where shaft 80 transitions from proximal portion 82 to distal portion 84. Proximal portion 82 of shaft 80 defines a circular cross-sectional configuration, which provides strength and support to shaft 80. The circular cross-sectional configuration of proximal portion 82, being smooth, continuous, without angles or edges, and radially-symmetric, also facilitates formation of a fluid-tight seal about proximal portion 82, e.g., via seal member 230 of cannula 200, upon insertion into cannula 200.

Distal portion 84 of shaft 80 and end effector assembly 100 cooperate to define a length "X" that is less than the overall cooperative length of shaft 80 and end effector assembly 100. Distal portion 84 defines a rectangular cross-sectional configuration including a pair of opposed short sides 85a and a pair of opposed long sides 85b. Each of the opposed long sides 85b of distal portion 84 of shaft 80 defines a width that approximates the diameter of the circular cross-sectional proximal portion 82 of shaft 80, although other configurations are also contemplated. Each of the opposed short sides 85a of distal portion 84 of shaft 80 defines a width that is less than a diameter of the circular cross-sectional proximal portion 82 of shaft 80 such that distal portion 84 of shaft 80 defines a narrowed configuration as compared to proximal portion 82 of shaft 80. This narrowed configuration facilitates visualization of end effector assembly 100 and insertion of end effector assembly 100 and shaft 80 through cannula 200 and into an internal surgical site, as detailed below. Further, the narrowed configuration of distal portion 84 of shaft 80 allows for positioning of other instrumentation, e.g., irrigation and/or suction tubes, a camera, a sensor(s), a light source, an energizable probe, a navigation tool, etc. alongside distal portion 84 of shaft 80 without extending beyond or extending minimally beyond the outer dimension of proximal portion 82 of shaft 80. The additional instrumentation may be incorporated into forceps 10, e.g., extending through proximal portion 82 of shaft 80 and alongside distal portion 84 of shaft 80, may be releasably engagable with distal portion 84 of shaft 80, or may be wholly separate from forceps 10.

Distal portion 84 of shaft 80 may be centered relative to the longitudinal axis "A-A" of shaft 80 or may be offset relative thereto, e.g., such that one of the long sides 85b is closer to the longitudinal axis "A-A" than the other long side 85b. Further, other narrowed configurations, e.g., square, oval, semi-circle, smaller-diametered circle, etc., are also contemplated. Intermediate portion 86 of shaft 80 provides a smooth, continuous transition between proximal and distal portions 82, 84, respectively, thus inhibiting potential snag points along shaft 80 and facilitating insertion thereof into and through cannula 200.

End effector assembly 100, as noted above, includes first and second jaw members 110, 120. Jaw members 110, 120 define curved configurations, wherein jaw members 110, 120 curve off of the longitudinal axis "A-A" of shaft 80 towards one of the long sides 85b of distal portion 84 of shaft 80 (and away from the other long side 85b of distal portion 84 of shaft 80). Jaw members 110, 120 are sufficiently curved such that the distal ends of jaw members 110, 120 extend beyond the outer dimension of the circular cross-sectional proximal portion 82 of shaft 80. Thus, the maximum width dimension defined by shaft 80 and end effector assembly 100 extends transversely from the distal tips "W1" of jaw members 110, 120 to the outer-most dimension of the opposite side "W2" of proximal portion 82 of shaft 80 (see FIG. 3). The curved configurations of jaw members 110, 120 of end effector assembly 100 facilitate visualization of tissue as tissue is grasped, manipulated, treated, and/or divided. In configurations where distal portion 84 of shaft 80 is offset relative to the longitudinal axis "A-A" of shaft 80, jaw members 110, 120 are configured to curve away from the offset direction of distal portion 84, thus reducing the maximum width dimension of shaft 80 and end effector assembly 100.

Referring to FIGS. 2 and 3, an exemplary cannula 200 configured for use in endoscopic surgery is shown defining a longitudinal axis "B-B" and generally including a proximal housing 210, a distal sleeve 220 extending from proximal housing 210, at least one seal member 230, and a fluid port 240 defined therein. Although exemplary cannula 200 is shown and described herein, it is understood that the aspects and features of the present disclosure apply equally to any suitable cannula providing access to an internal surgical site. Proximal housing 210 is configured for positioning on the exterior surface of a patient's skin and includes seal member 230 disposed therein. Proximal housing 210, distal sleeve 220, and seal member 230 cooperate to define a lumen 225 extending therethrough. Seal member 230 is configured to establish a fluid-tight seal about an instrument or instruments, e.g., proximal portion 82 of shaft 80 of forceps 10 (FIG. 1), inserted through lumen 225 of cannula 200. Seal member 230 may be any suitable seal or combination of seals, e.g., a duck bill valve, brush seal, elastomeric seal, etc., for establishing a fluid-tight seal about an instrument or instruments. Fluid port 240 is configured to connect to a fluid supply for insufflating the internal surgical site, providing other fluid thereto, or removing fluid therefrom. Cannula 200 defines a length "Y" and lumen 225 of cannula 200 defines a diameter "D." Further, plural cannulas 200 may be provided of different lengths and/or diameters, such that an appropriate cannula 200 may be selected based upon a patient's anatomy, the procedure to be performed, preference of the user, and/or other factors. To this end, plural forceps 10 may be provided, each configured for use with one or more of the different length and/or diameter cannulas 200. It is typically advantageous to use the smallest-diametered cannula 200 suitable for the particular patient and/or procedure as such requires a smaller incision for the cannula 200 and, as a result, reduced post-surgical pain and healing time. However, other factors and/or considerations may warrant use of a different cannula 200.

Referring to FIG. 3, as noted above, shaft 80 and end effector assembly 100 are configured for insertion through cannula 200 and into an internal surgical site. Where plural size cannulas 200 and/or forceps 10 (FIG. 1) with plural size shafts 80 are provided, a suitable cannula 200 and forceps 10 (FIG. 1) pair is first selected. In an effort to utilize the smallest-diameter cannula 200, it is contemplated that the cannula 200 and forceps 10 (FIG. 1) pair be configured such that the length "Y" of the cannula 200 is equal to the collective length "X" of distal portion 84 of shaft 80 and end effector assembly 100 or less than the collective length "X" but sufficiently long so as to ensure that seal member 230 is disposed about proximal portion 82 of shaft 80 when end effector assembly 100 is positioned within the internal surgical site (rather than being disposed about transition portion 86 or distal portion 84, where it may be more difficult to establish an effective seal). For similar purposes, it is further contemplated that cannula 200 and forceps 10 (FIG. 1) be configured such that the diameter "D" of lumen 225 of cannula 200 is equal to or greater than the maximum width dimension defined by shaft 80 and end effector assembly 100 but sufficiently small to enable insertion of end effector assembly 100 and shaft 80 therethrough in an angled orientation relative to distal sleeve 220 of cannula 200.

In use, cannula 200 is positioned within an opening in tissue such that proximal housing 210 remains external while distal sleeve 220 extends through the opening in tissue into the internal surgical site. When forceps 10 (FIG. 1) is to be used, end effector assembly 100 and shaft 80 are inserted through lumen 225 of cannula 200. As a result of the above-noted length and width/diameter relationship, end effector assembly 100 and distal portion 84 of shaft 80 are inserted through lumen 225 of cannula 200 in an angled orientation relative to longitudinal axis "B-B" of cannula 200. This configuration enables insertion of end effector 100 and distal portion 84 of shaft 80 through lumen 225 of cannula 220 despite diameter "D" of lumen 225 of cannula 200 being equal to or greater than the maximum width dimension defined by shaft 80 and end effector assembly 100. As end effector assembly 100 and shaft 80 are further inserted through lumen 225 of cannula 200, the distal tips "W1" of jaw members 110, 120 eventually reach the distal end of distal sleeve 220 of cannula 200. As a result of the length "Y" of the cannula 200 being equal to or less than the collective length "X" of distal portion 84 of shaft 80 and end effector assembly 100, the distal tips "W1" of jaw members 110, 120 reach the distal end of distal sleeve 220 prior to transition portion 86 of shaft 80 entering lumen 225 of cannula 200. Thus, upon further insertion of end effector assembly 100 and shaft 80 into cannula 200, curved jaw members 110, 120 begin to emerge from the distal end of distal sleeve 220, allowing shaft 80 to be straightened from the angled orientation towards an aligned orientation relative to longitudinal axis "B-B" of cannula 200, thereby providing sufficient clearance for transition portion 86 and, ultimately, proximal portion 82 of shaft 80 to enter lumen 225 of cannula 200 to permit further insertion of end effector assembly 100 and shaft 80 into and through cannula 200 such that end effector assembly 100 may be readily positioned at the internal surgical site.

With end effector assembly 100 positioned at the internal surgical site, at least a portion of proximal portion 82 of shaft 80 has entered cannula 200 such that seal member 230 is disposed about the circular cross-sectional proximal portion 82 of shaft 80, thus ensuring an effective fluid-tight seal. Once this position has been achieved, forceps 10 (FIG. 1) may be utilized to grasp, treat, and/or divide tissue, as detailed below.

Referring to FIGS. 1 and 8B, end effector assembly 100, as mentioned above, includes first and second jaw members 110, 120. Jaw members 110, 120 are pivotably coupled to one another and shaft 80 to enable movement of jaw members 110, 120 relative to one another and shaft 80 between the spaced-apart position and the approximated position. As an alternative to this bilateral configuration, end effector assembly 100 may define a unilateral configuration, e.g., wherein jaw member 120 is fixed relative to shaft 80 and jaw member 110 is pivotable relative to jaw member 120 and shaft 80 between the spaced-apart and approximated positions.

Each jaw member 110, 120 of end effector assembly 100 includes a proximal flange 111, 121 and a distal body 112, 122. Proximal flanges 111, 121 define aligned pivot apertures (not shown) and oppositely-angled cam slots 113, 123. The pivot apertures are configured to receive a pivot pin 103 for pivotably coupling jaw members 110, 120 to clevis 88 of distal portion 86 of shaft 80. Oppositely-angled cam slots 113, 123 receive a drive pin 105 that is operably coupled to drive bar 132 of drive assembly 130 (FIGS. 6A-6C) such that translation of drive bar 132 through shaft 80 and relative to end effector assembly 100 pivots jaw members 110, 120 between the spaced-apart and approximated positions.

Distal bodies 112, 122 of jaw members 110, 120 each define a curved configuration, as noted above, wherein distal bodies 112, 122 curve laterally in similar directions. Distal jaw bodies 112, 122 each further define opposing tissue-contacting surfaces 116, 126. Tissue-contacting surfaces 116, 126 are formed at least partially from an electrically-conductive material and either or both are adapted to connect to a source of energy as well as activation assembly 180 (FIGS. 6A-6C) via the lead wires extending through cable 2 (FIG. 1) to enable the selective supply of energy thereto for treating tissue grasped therebetween. Either or both of distal bodies 112, 122 may further define a knife channel 118, 128 extending through tissue-contacting surfaces 116, 126 to facilitate reciprocation of knife 162 between jaw members 110, 120.

Turning to FIGS. 1, 4, and 6A-6C, handle assembly 30 includes movable handle 40, fixed handle portion 50 of housing 20, and a linkage 44. Movable handle 40 is pivotably coupled to housing 20 within housing 20 to enable pivoting of movable handle 40 relative to fixed handle portion 50 between an initial position (FIG. 1) and a compressed position (FIG. 8A). Linkage 44 operably couples movable handle 40 with drive assembly 130 such that pivoting of movable handle 40 between the initial and compressed positions translates drive bar 132 (FIGS. 6C and 8B) through shaft 80 and relative to end effector assembly 100 to move jaw members 110, 120 between the spaced-apart position and the approximated position. Drive assembly 130 may further include a spring mandrel assembly 134 (FIGS. 6A-6C) operably coupling linkage 44 with drive bar 132 such that a closure pressure imparted to tissue grasped between jaw members 110, 120 is limited to a particular closure pressure range, e.g., between about 3 kg/cm$^2$ and about 16 kg/cm$^2$.

Movable handle 40 and fixed handle portion 50 further include cooperating engagement components 48, 58, respectively, e.g., a pin and corresponding track, to enabling locking of movable handle 40 in the compressed position upon achieving the compressed position, thereby retaining the jaw members 110, 120 in the approximated position. Cooperating engagement components 48, 58 may be disengaged, allowing movable handle 40 to return to the initial position, upon moving movable handle 40 further towards fixed handle portion 50 to an over-compressed position and then releasing or returning movable handle 40 towards the initial position.

With reference to FIGS. 1 and 4-6C, trigger assembly 60 includes a trigger 62, an elongated link 68a, and a lever arm 68b. Trigger 62 includes a toggle 63 and a disc body 66. Toggle 63 includes an upper flange 64a and a manipulation portion 65a extending from upper flange 64a. Upper flange 64a of toggle 63 includes disc body 66 rotatably coupled thereabout. Upper flange 64a further includes an activation post 64b extending from each lateral side thereof. As detailed below, one of the ends 64c of activation post 64b is configured to depress the corresponding switch 182 of activation assembly 180 (depending upon the direction of activation of trigger 62, as detailed below) to supply energy to jaw members 110, 120. Switches 182 may be configured as dome switches or other suitable switches to facilitate activation thereof via activation posts 64b. Switches 182 may be configured to produce an audible and/or tactile "click" upon activation, thus indicating to a user that energy is being supplied to end effector assembly 100 (FIG. 8B).

Manipulation portion 65a of toggle 63 of trigger 62 extends from housing 20 and defines a distally-facing contact surface 65b and a pair of side wing surfaces 65c extending from either side of distally-facing contact surface 65b in a proximal direction. Distally-facing contact surface 65b is configured to facilitate actuation of trigger 62, e.g., proximal pivoting of trigger 62 from an un-actuated position (FIG. 1) to an actuated position (FIG. 8B), to deploy knife 162 relative to end effector assembly 100 (see FIG. 8B). Side wing surfaces 65c are configured to facilitate activation of trigger 62, e.g., lateral pivoting of trigger 62 (in either lateral direction) from a neutral position (FIG. 1) to an activated position (FIG. 7), for urging one of the ends 64c of activation post 64b into the corresponding switch 182 of activation assembly 180 (depending upon the direction of activation of trigger 62) to activate the switch 182 and supply energy to jaw members 110, 120. Further, side wing surfaces 65c are configured to surround movable handle 40 in the initial position of movable handle 40 (see FIG. 4) such that lateral pivoting of trigger 62 from the neutral position is inhibited when jaw members 110, 120 are disposed in the spaced-apart position (see FIG. 1). As such, side wing surfaces 65c of trigger 62 and movable handle 40 cooperate to define a lockout that inhibits energy from being supplied to jaw members 110, 120 when jaw members 110, 120 are disposed in the spaced-apart position.

Figure 4:
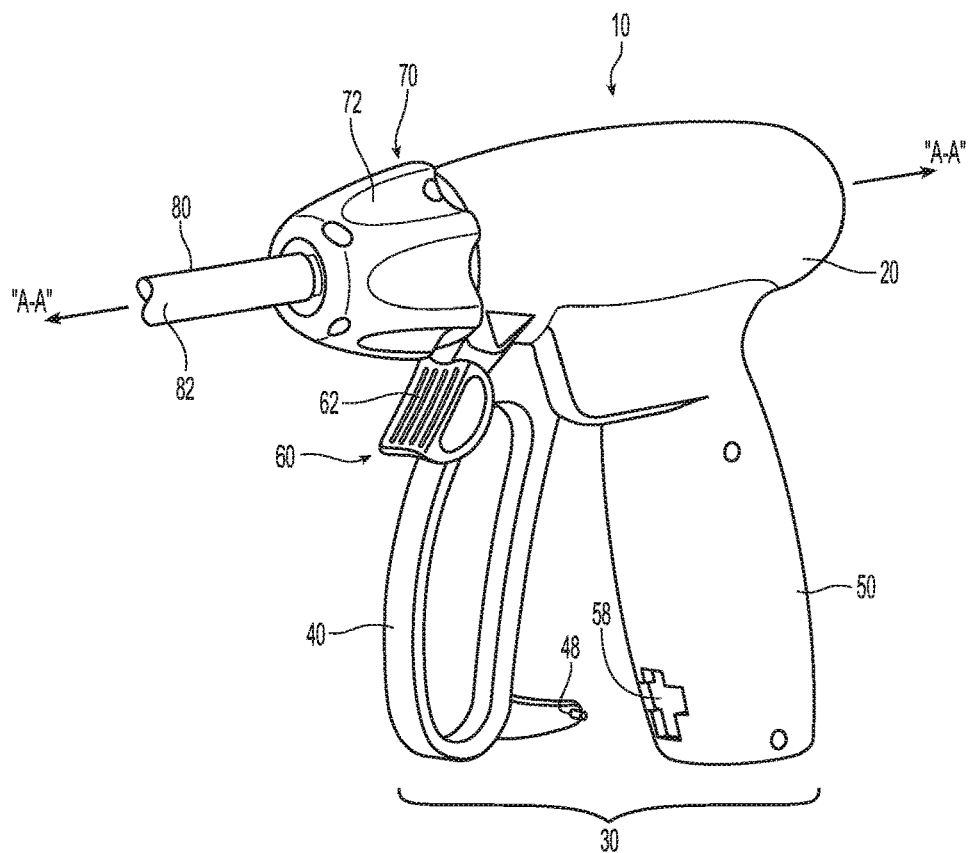
FIG. 4 is a perspective view of a proximal portion of the surgical forceps of FIG. 1.
Figure 5A:
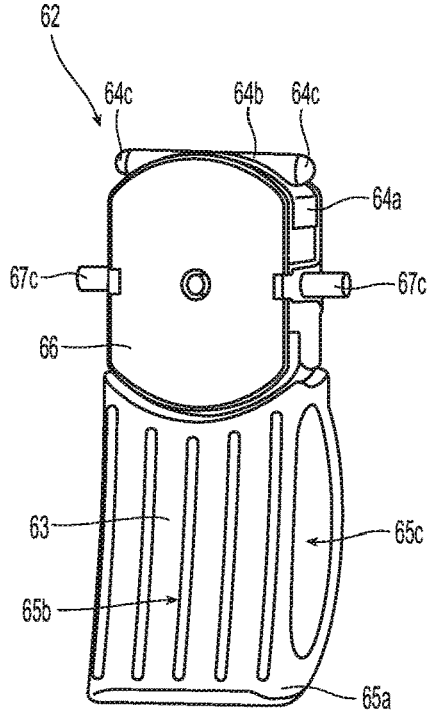
FIG. 5A is a front, perspective view of the trigger of the surgical forceps of FIG. 1.
Figure 5B:
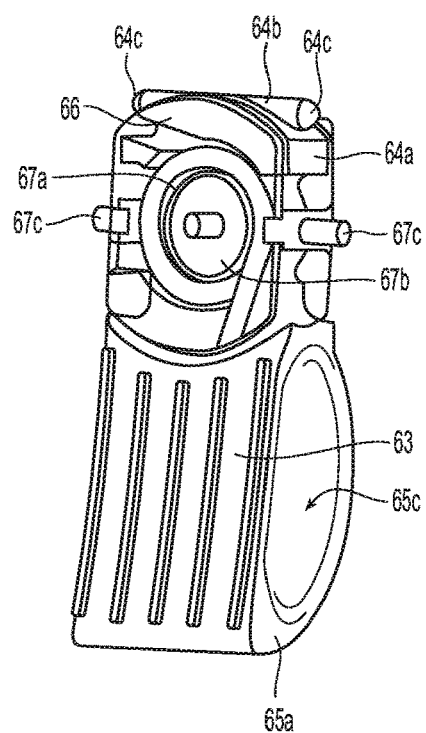
FIG. 5B is a rear, perspective view of the trigger of the surgical forceps of FIG. 1.
Figure 7:
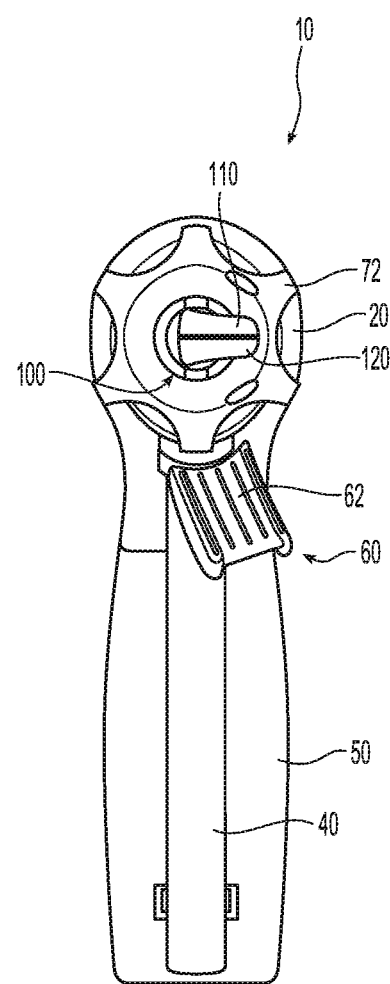
FIG. 7 is a front view of the surgical forceps of FIG. 1, with the trigger disposed in an activated position.

Disc body 66 of trigger 62, as noted above, is rotatably coupled about upper flange 64a. More specifically, disc body 66 includes a circular pivot aperture 67a received within a circular pivot member 67b defined within upper flange 64a of toggle 63 such that toggle 63 is laterally pivotable relative to disc body 66, e.g., between the neutral and activated positions (FIGS. 4 and 7, respectively). Disc body 66 further includes a pair of outwardly-extending pivot posts 67c configured for receipt within corresponding pivot apertures 22 (FIG. 6C, only one of apertures 22 is shown) defined within housing 20 to pivotably couple trigger 62 to housing 20. As such, trigger 62 is pivotably actuatable relative to housing 20, via the pivotable coupling of pivot posts 67c within pivot apertures 22, between the un-actuated position (FIG. 1) and the actuated position (FIG. 8A).

Referring to FIGS. 6A-6C, as noted above, trigger assembly 60 further includes an elongated link 68a and a lever arm 68b. Elongated link 68a is pivotably coupled to disc body 66 of trigger 62 at the distal end of elongated link 68a and is pivotably coupled to lever arm 68b at the proximal end of elongated link 68a. Lever arm 68b is pivotably coupled to housing 20 at a first end thereof, is operably coupled to proximal collar 164 of knife assembly 160 at a second end thereof. Proximal collar 164 is engaged about the proximal end of knife bar 166, which extends distally through housing 20 and a portion of shaft 80. Knife 162 (FIG. 8B) is engaged with and extends distally from knife bar 166. As a result of the above-detailed configuration, proximal actuation of trigger 62 from the un-actuated position (FIG. 1) to the actuated position (FIG. 8A) translates knife 162 distally to the extended position (FIG. 8B), wherein knife 162 extends between jaw members 110, 120.

As illustrated in FIGS. 6A and 6B, housing 20 may further define lock surfaces 24 positioned to interfere with activation post 64b of toggle 63 of trigger 62 in the activated position thereof such that actuation of trigger 62 from the un-actuated position to the actuated position is inhibited when trigger 62 is disposed in the activated position. Thus, knife 162 (FIG. 8B) is inhibited from being deployed while energy is being supplied to jaw members 110, 120 of end effector assembly 100 (see FIG. 8B). Likewise, when trigger 62 is disposed in the actuated position (FIG. 8A), activation posts 64b are positioned adjacent an interior surface of housing 20 and spaced-apart from switches 182, inhibiting lateral pivoting of trigger 62, thereby inhibiting energy activation when knife 162 is deployed.

Referring generally to FIGS. 1 and 4-8B, in use, once end effector assembly 100 is positioned adjacent an internal surgical site, e.g., through cannula 200 (FIGS. 2 and 3), as detailed above, forceps 10 may be manipulated, e.g., via moving housing 20 and/or rotating rotation nose 72 of rotation assembly 70, such that jaw members 110, 120 of end effector assembly 100 are positioned with tissue to be grasped, treated, and/or divided therebetween. Thereafter, jaw members 110, 120 may be moved from the spaced-apart position to the approximated position to grasp tissue by moving movable handle 40 from the initial position (FIG. 1) to the compressed position (FIG. 8A).

With tissue grasped between jaw members 110, 120 of end effector assembly 100, trigger 62 may be activated by laterally pivoting trigger 62 from the neutral position (FIG.

1) to either of the activated positions (e.g., the activated position illustrated in FIG. 7) to thereby activate the corresponding switch 182 of activation assembly 180. The activation of either switch 182 supplies energy from the energy source to tissue-contacting surfaces 116, 126 (FIG. 8B) of jaw members 110, 120 to treat tissue grasped therebetween.

Once tissue has been sufficiently treated, or where it is only desired to grasp and divide tissue, with trigger 62 disposed in (or returned to) the neutral position, trigger 62 may be pivoted proximally from the un-actuated position to the actuated position to thereby deploy knife 162 (FIG. 8B) between jaw members 110, 120 to cut tissue grasped therebetween. The treated and/or divided tissue may be released by releasing or returning movable handle 40 to the initial position and subsequent tissue may then be grasped, treated, and/or divided similarly as detailed above.

The above-detailed aspects and features of the present disclosure may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 9:
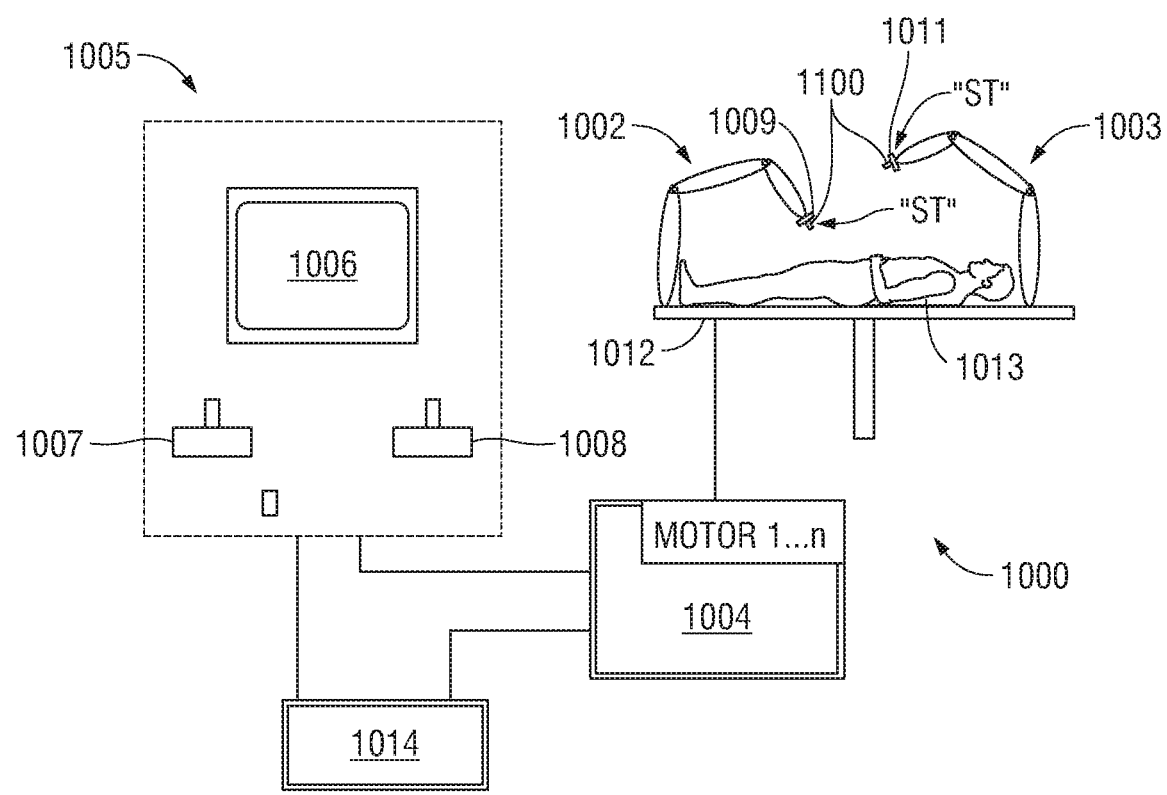
FIG. 9 is a schematic illustrating of a robotic surgical system configured for use in accordance with aspects of the present disclosure.

Turning to FIG. 9, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100. Suitable surgical tools "ST" include forceps 10, and end effector assembly 100 thereof (see FIG. 1).

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. A surgical instrument, comprising:
a housing;
a shaft extending distally from the housing;
an end effector assembly disposed at a distal end of the shaft, the end effector assembly adapted to connect to a source of energy to supply energy to tissue to treat tissue;
a knife slidably disposed within the shaft and movable relative to the end effector assembly between a retracted position and an extended position; and
a trigger operably coupled to the housing, the trigger selectively activatable from a neutral position to a laterally pivoted position to supply energy to the end effector assembly, and selectively actuatable from a distal position to a proximally pivoted position to deploy the knife from the retracted position to the extended position, wherein, in the laterally pivoted position, proximal actuation of the trigger from the laterally pivoted position is mechanically inhibited, and wherein, in the proximally pivoted position, activation of the trigger is mechanically inhibited.

2. The surgical instrument according to claim 1, wherein the trigger includes a toggle and a disc body, the disc body pivotably coupled to the housing to permit actuation of the trigger from the distal position to the proximally pivoted position, the toggle pivotably coupled to the disc body and pivotable relative thereto for activating the trigger from the neutral position to the laterally pivoted position.

3. The surgical instrument according to claim 1, wherein the trigger is selectively activatable from the neutral position to first and second opposed laterally pivoted positions.

4. The surgical instrument according to claim 1, wherein the trigger defines a distally-facing surface configured to facilitate manual manipulation of the trigger from the distal position to the proximally pivoted position.

5. The surgical instrument according to claim 4, wherein the trigger defines a pair of side wing surfaces extending from opposing sides of the distally-facing surface, the side wing surfaces configured to facilitate manual manipulation of the trigger from the neutral position to the laterally pivoted position.

6. The surgical instrument according to claim 1, wherein the end effector assembly includes first and second jaw members, at least one of the first or second jaw members movable relative to the other between a spaced-apart position and an approximated position.

7. The surgical instrument according to claim 6, further comprising a movable handle operably coupled to the housing, the movable handle movable between an initial position and a compressed position for moving the at least one of the first or second jaw members between the spaced-apart position and the approximated position.

8. The surgical instrument according to claim 7, wherein, in the initial position of the movable handle, the movable handle interferes with the trigger to inhibit activation of the trigger from the neutral position towards the laterally pivoted position.

9. The surgical instrument according to claim 1, further comprising an activation assembly including at least one switch disposed within the housing, the at least one switch positioned such that, upon activation of the trigger from the neutral position to the laterally pivoted position, a portion of the trigger activates the at least one switch.

10. The surgical instrument according to claim 9, wherein the at least one switch is a dome switch configured to produce at least one of an audible or tactile output in response to activation thereof.

11. A surgical instrument, comprising:
a housing;
a shaft extending distally from the housing;
an end effector assembly disposed at a distal end of the shaft, the end effector assembly including first and second jaw members adapted to connect to a source of energy to supply energy to tissue to treat tissue, at least one of the first or second jaw members movable relative to the other between a spaced-apart position and an approximated position;
a movable handle operably coupled to the housing and movable relative thereto between an initial position and a compressed position to move the at least one of the first or second jaw members between the spaced-apart position and the approximated position;
a knife slidably disposed within the shaft and movable between a retracted position and an extended position, wherein the knife extends at least partially between the first and second jaw members; and
a trigger operably coupled to the housing, the trigger laterally pivotable to a laterally pivoted position to supply energy to the first and second jaw members and proximally pivotable to move the knife from the retracted position to the extended position, wherein, in the initial position of the movable handle, at least a portion of the movable handle interferes with the trigger to mechanically inhibit lateral pivoting thereof, and wherein in the laterally pivoted position, proximal actuation of the trigger from the laterally pivoted position is mechanically inhibited.

12. The surgical instrument according to claim 11, wherein the trigger includes a toggle and a disc body, the disc body pivotably coupled to the housing to permit proximal pivoting of the trigger, the toggle pivotably coupled to the disc body and pivotable relative thereto to permit lateral pivoting of the trigger.

13. The surgical instrument according to claim 11, wherein the trigger is laterally pivotable in either direction from a neutral position to a laterally pivoted position to supply energy to the first and second jaw members.

14. The surgical instrument according to claim 11, wherein the trigger defines a distally-facing surface configured to facilitate proximal pivoting of the trigger.

15. The surgical instrument according to claim 14, wherein the trigger defines a pair of side wing surfaces extending from opposing sides of the distally-facing surface, the side wing surfaces configured to facilitate lateral pivoting of the trigger, and wherein, in the initial position of the movable handle, the side wing surfaces at least partially surround the movable handle.

16. The surgical instrument according to claim 11, further comprising a drive assembly operably coupled between the end effector assembly and the movable handle such that movement of the movable handle from the initial position to the compressed position moves the at least one of the first or second jaw members from the spaced-apart position to the approximated position.

17. The surgical instrument according to claim 11, further comprising at least one linkage operably coupled between the trigger and the knife such that proximal pivoting of the trigger moves the knife from the retracted position to the extended position.

18. The surgical instrument according to claim 11, wherein the knife defines a distal cutting edge having a dual rake configuration.

19. The surgical instrument according to claim 11, further comprising an activation assembly including at least switch disposed within the housing, the at least one switch positioned such that, upon lateral pivoting of the trigger, the trigger activates the at least one switch to supply energy to the first and second jaw members.

20. The surgical instrument according to claim 11, wherein a first portion of the housing interferes with the trigger to inhibit proximal pivoting of the trigger when the trigger is laterally pivoted, and wherein a second portion of the housing interferes with the trigger to inhibit lateral pivoting of the trigger when the trigger is proximally pivoted.

* * * * *